United States Patent [19]
Yarger

[11] 3,952,751
[45] Apr. 27, 1976

[54] HIGH-PERFORMANCE ELECTROTHERAPEUTIC APPARATUS

[75] Inventor: Frank A. Yarger, Harbor City, Calif.

[73] Assignee: W. Denis Kendall, Los Angeles, Calif.

[22] Filed: Jan. 8, 1975

[21] Appl. No.: 539,283

[52] U.S. Cl. ............................................. 128/422
[51] Int. Cl.² ........................................... A61N 1/40
[58] Field of Search .......... 128/405, 404, 413, 421, 128/422

[56] References Cited
UNITED STATES PATENTS

| | | | |
|---|---|---|---|
| 3,299,892 | 1/1967 | Kendall et al. | 128/421 |
| 3,513,851 | 5/1970 | Smith et al. | 128/422 |
| 3,566,877 | 3/1971 | Smith et al. | 128/404 |
| 3,800,802 | 4/1974 | Berry et al. | 128/422 |

FOREIGN PATENTS OR APPLICATIONS

| | | | |
|---|---|---|---|
| 679,371 | 2/1964 | Canada | 128/404 |

*Primary Examiner*—Robert W. Michell
*Assistant Examiner*—Lee S. Cohen
*Attorney, Agent, or Firm*—William W. Haefliger

[57] ABSTRACT

Improved electrotherapeutic apparatus comprises a. an electromagnetic energy radiating head including primary and secondary coils and a capacitor electrically connected across the secondary coil, b. and an input circuit including a source of high frequency oscillations, a power amplifier and a control circuit for creating and transmitting to the head a sequence of pulses of high frequency electrical energy and for controlling the amplitude of the pulses and the intervals therebetween, the pulses having substantially rectangular shape and having a repetition rate and duration characterized in that they define a duty factor of between 0.35 and 0.55, where (duty factor) = (pulse repetition rate in pulses per second) × (pulse duration in micro seconds).

8 Claims, 6 Drawing Figures

HIGH-PERFORMANCE ELECTROTHERAPEUTIC APPARATUS

BACKGROUND OF THE INVENTION

This invention relates generally to electrotherapeutic apparatus, and more particularly concerns improvements in apparatus to generate, control and transmit pulses of high frequency electromagnetic radiation, for application to a patient by means of a treatment head. Such improvements are related to prior apparatus of the type described in prior Kendall and Yarger U.S. Patents.

Prior circuits to generate control and transmit such pulses suffered certain disadvantages. For example, the duty cycles of the pulses, and as defined herein, were relatively low so that the effectiveness and efficiency of the treatment was less than desirable. Also, diamond-shaped or saw-toothed pulses as exemplified in U.S. Pat. No. 3,566,877 to Smith, as well as pulses produced by other devices, contained insufficient pulse energy. Further, the power amplifier stages of prior devices could not adequately handle changes in load current induced by changes in coupling of the treatment head to body loads. Further, harmonics and spurious signals were produced at the input to the power stage, causing difficulty in maintaining good regulation and the required 27.12 megacycle frequency at the head.

SUMMARY OF THE INVENTION

It is a major object of the invention to provide apparatus overcoming the above as well as other problems and disadvantages associated with prior apparatus. Basically, and as regards the optimizing of pulsed energy output, the invention is embodied in apparatus that includes:

a. an electromagnetic energy radiating head including primary and secondary coils and a capacitor electrically connected across the secondary coil, b. and input circuit means including a source of high frequency oscillations, power amplifier and control means for creating and transmitting to the head a sequence of pulses of high frequency electrical energy and for controlling the amplitude of the pulses and the intervals therebetween, the pulses having substantially rectangular shape and having a repetition rate and duration characterized in that they define a duty factor of between 0.35 and 0.55, where (duty factor) = (pulse repetition rate in pulses per second) × (pulse duration in micro seconds).

As will appear, the duty factor is desirably about 0.45, and the power amplifier means comprises multiple ceramic type vacuum tubes, to overcome load current problems as described. Further, a series resonant circuit is provided at the input to the power amplifier to eliminate spurious signals and harmonics.

These and other objects and advantages of the invention, as well as the details of an illustrative embodiment, will be more fully understood from the following detailed description of the drawings, in which:

DRAWING DESCRIPTION

DETAILED DESCRIPTION

Figure 1:
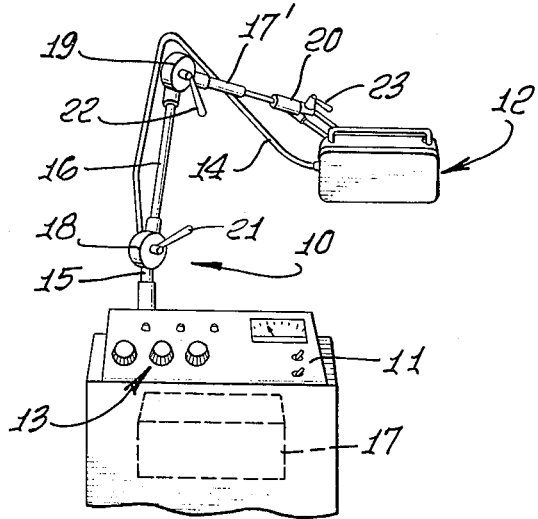
FIG. 1 is an elevation showing electrotherapeutic equipment with which the invention is associated.

In FIG. 1, an arm assembly 10 is seen in combination with a cabinet top 11, and an electrotherapeutic treatment head 12, the latter supported by the arm assembly. Controls 13 located on the cabinet top may be manipulated for controlling the amplitude and recurrence interval of pulses supplied to the head. A high voltage coaxial cable 14 runs from the electrical apparatus 17 contained in the cabinet, and to the head. Typically, pulses transmitted by apparatus 17 are made up of bursts of signal frequencies of about 27.12 megacycles, the pulse recurrence interval being, for example from 333 microseconds to 1.25 milliseconds. Arm assembly 10 includes post 15, arm sections 16 and 17', and hinge joints 18 and 19 located as shown to interconnect the post and arm sections, there being locking handles 21 and 22 associated with the joints to lock the arm sections at selected relative angles as determined by the location of head 12. Joint 20 and associated locking handle 23 control pivoting of the head about an axis defined by arm section 17'.

The head 12 basically comprises a shell (as for example at 24); spaced apart inductively coupled primary and secondary coils (as at 25 and 26, for example) carried by the shell to face forwardly, the primary coil adapted to be supplied with pulsed electrical energy as from cable 14, and the secondary coil adapted to radiate electromagnetic energy generally forwardly; and a capacitor 30 carried within the shell to have electrical parallel connection with one of the coils, as for example the secondary coil.

Figure 3:
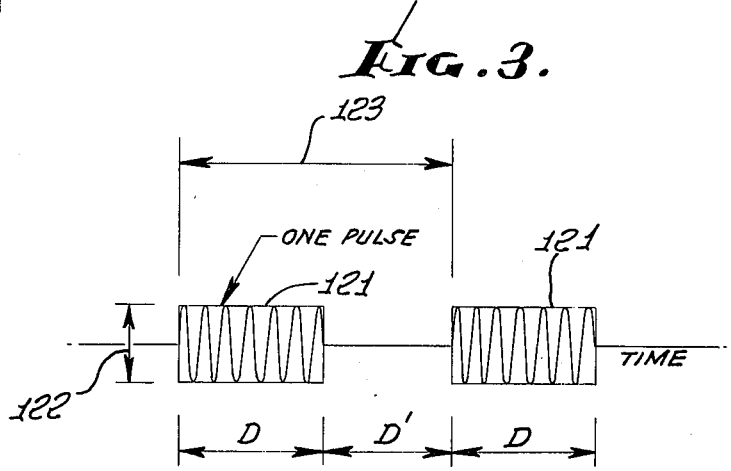
FIG. 3 is a pulse wave form.
Figure 4:
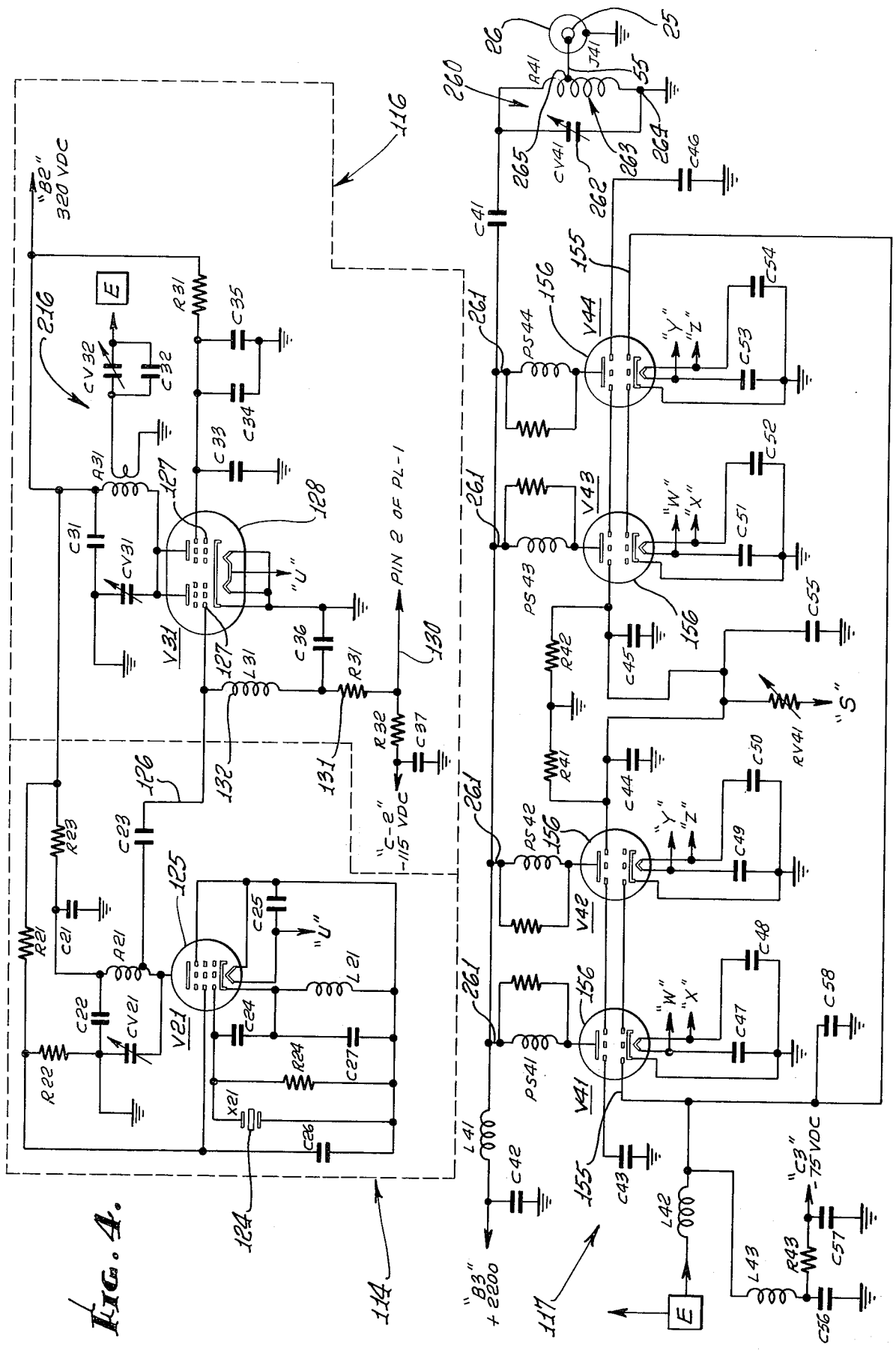
FIGS. 4–6 are electrical circuit diagrams.
Figure 5:
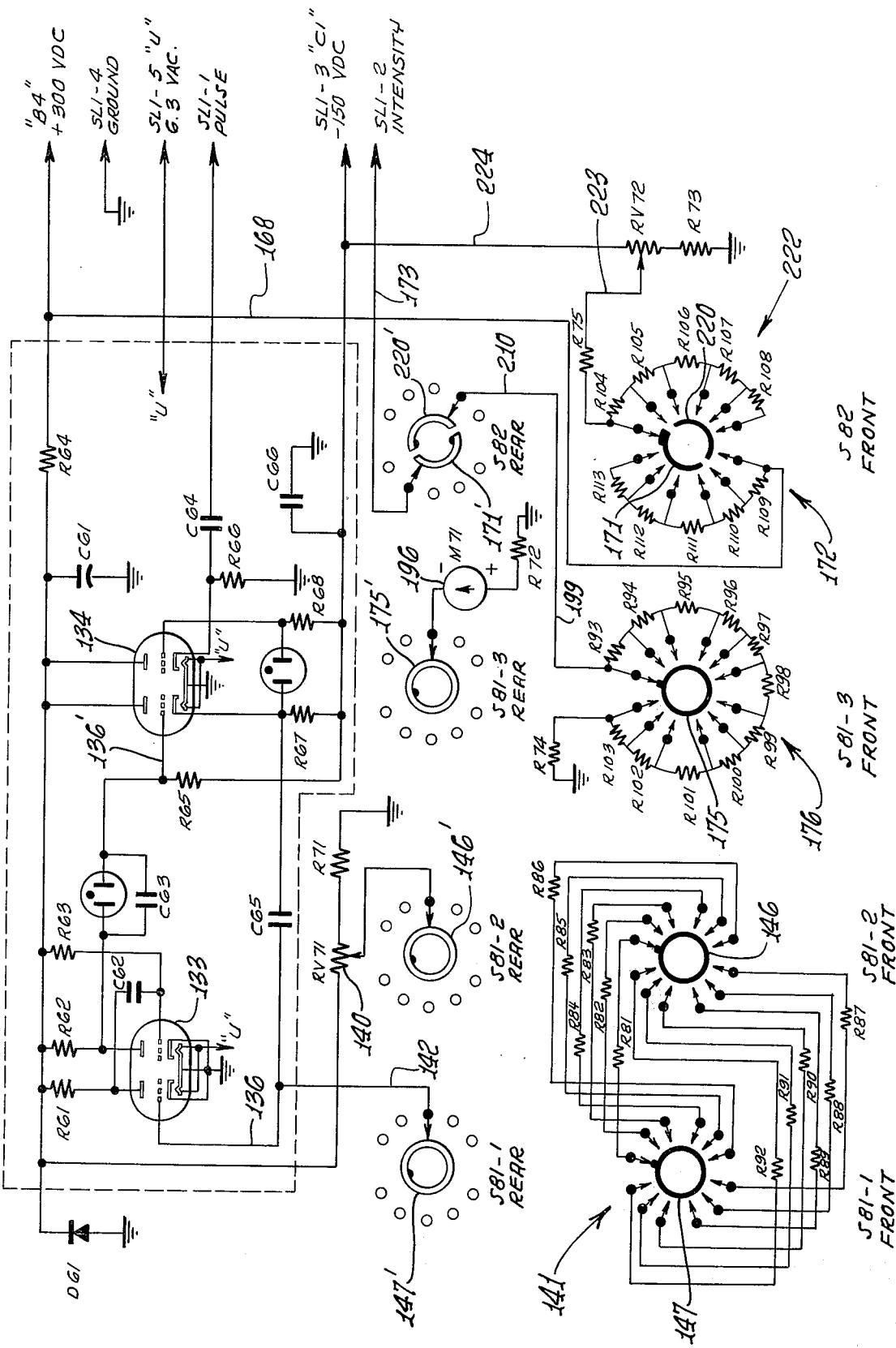

FIGS. 4 and 5 illustrate the provision of input circuit means, including a source 114 and 116 of high frequency oscillations, power amplifier 117 and control means (see FIG. 5) for creating and transmitting to the head (i.e., to primary coil 25 in FIG. 4) a sequence of pulses of high frequency electrical energy, and for controlling the amplitude of the pulses and the intervals therebetween. As shown in FIG. 3, the like power pulses 121 have rectangular envelope shape, and each is made up of a high frequency signal burst having a selected amplitude 122. Pulse duration is indicated at D, and the intervals between pulses appear at D'. As will appear, an important aspect of the invention concerns the provision for a duty factor of between 0.35 and .55, and preferably about 0.45, where duty factor is a product defined as:

(DUTY FACTOR) = (pulse repetition rate in pulses per second) × (pulse duration D in micro seconds).

Also, the signal high frequency is 27.12 megacycles. Accordingly, highly efficient and effective radiation from the head is achieved.

Referring again to FIG. 4, the source of oscillation includes oscillator means 114 shown to include a crystal 124 for establishing a desired high frequency oscillation, say 6.780 megacycles; this frequency is applied to the tube 125 and doubled to 13.56 megacycles for transmission at 126 to the amplifier - doubler 116, and in particular to the grids 127 of tube 128. Amplifier - doubler 116 doubles the frequency to the value 27.12 megacycles which is transmitted via series resonant circuit 216 to the power amplifier 117 (see terminals E). Circuit 216 eliminates second harmonics and spurious signals from the stages 114 and 116. Amplifier - doubler 116 also transmits the high frequency in pulses 121, as previously described, as established by the switching pulse at 130, coupled to lead 126 via resistor 131 and coil 132.

The switching pulse is obtained from the SL1-1 output of the multivibrator, including tube 133 and cathode follower stage 134, as shown in FIG. 5. See also corresponding terminals 1 of SL-1 and 2 of PL-1 in FIG. 6.

The multivibrator has a grid input shown at 136, the voltage of which is variable, and preferably stepwise variable, to provide selection of pulse interval 123, as indicated in FIG. 3, and which equals D+D'. The preferred interval may be varied in ten or twelve steps, within the range 0.33 milliseconds to 1.25 milliseconds, in order to increase or decrease the intensity of treatment given the patient.

A highly desirable manually controllable step controller for the multivibrator is shown in FIG. 5 to comprise a circuit that includes B4 voltage lead, resistor 140, step resistance selector 141 providing voltage scaler or divider means, and lead 142 connected to grid inputs 136 of tube 133. As shown in FIG. 5, device 141 includes a series of resistors R81-R92 which are alternately or selectively connectible between ganged rotary terminals 146 and 147. The rear side 146' of terminal 146 is tap connected with resistor 140, and the rear side 147' of terminal 147 is connected via lead 142 with the grid input 136. Accordingly, as terminals 146 and 147 are manually rotated, different voltages are applied to the grid inputs 136 and 136' of the multivibrator for pulse interval control. The plates of the multivibrator are also supplied with voltage as by B4 lead.

Figure 2:
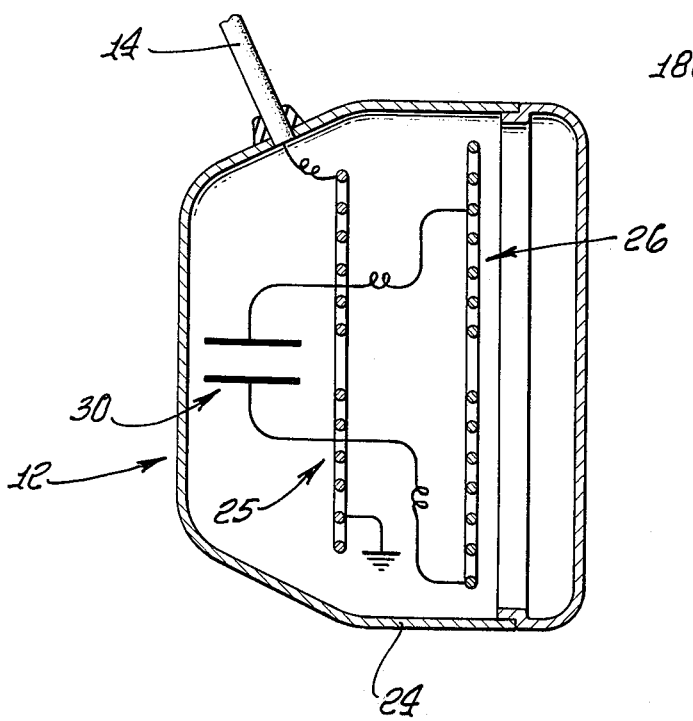
FIG. 2 is an enlarged vertical side elevation taken in section through treatment head structure.
Figure 6:
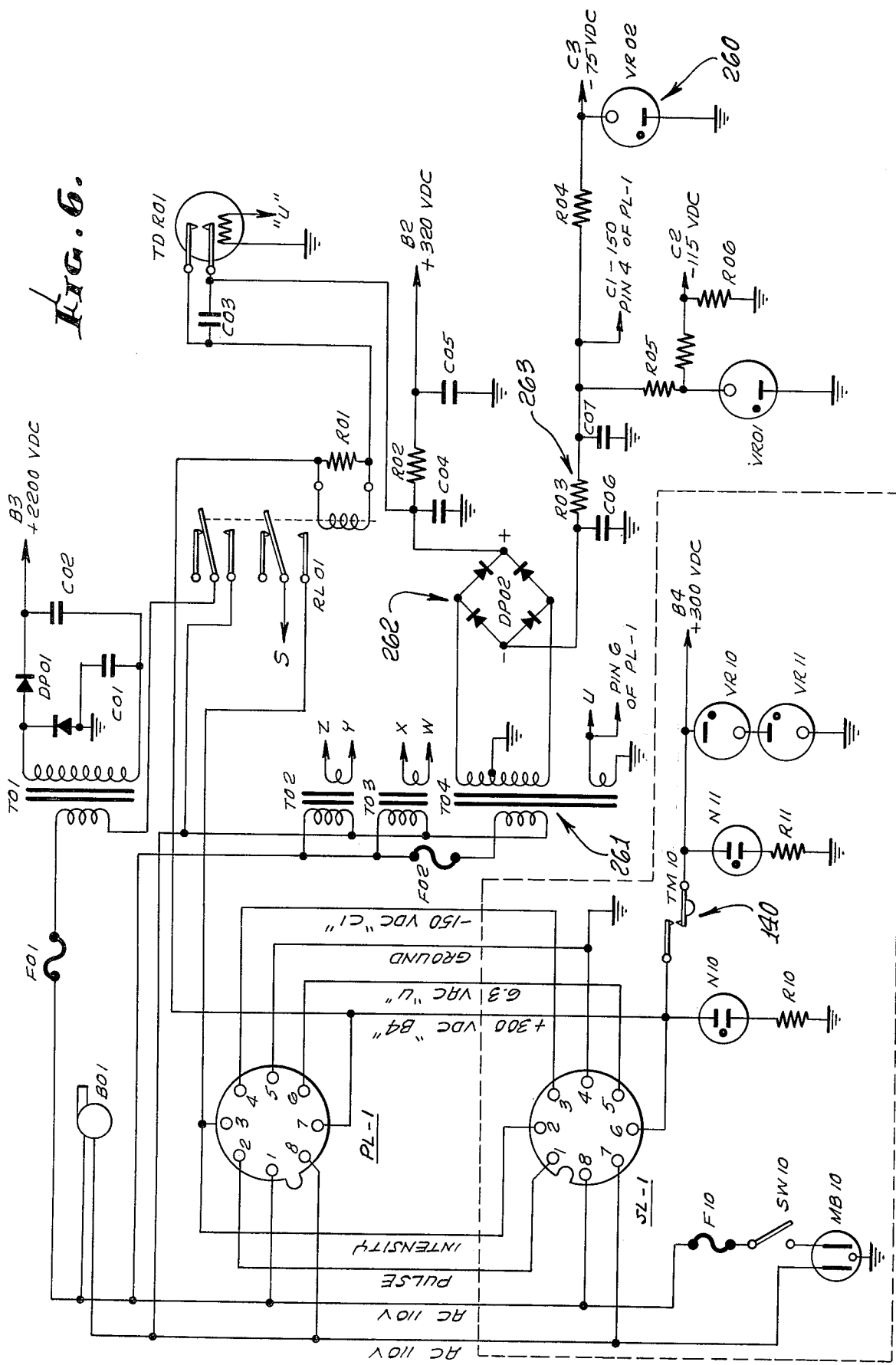

Turning back to FIG. 4, the signal output at $\boxed{E}$ is applied to the grids 155 of the four power amplifier tubes 156, for pulse power amplification. In this connection, the plates of those tubes are suitably supplied with high voltage, for example 2200 volts DC from point B3. See in this regard the power supply shown in FIG. 6. FIG. 4 shows the grids of tubes 156 as having input from point "S", also shown in FIG. 6, that point connected (via a pulse amplitude control circuitry) with positive voltage source B4. For example, from that source, direct current flows, in FIG. 5, via lead 168, selected resistors R109--R113 and rotary terminals 171 and 171' of scaler 172, lead 173 to terminal SL-1-2 in FIGS. 5 and 6, then to "S." Accordingly, upon manual turning of the terminals 171 and 171', a selected voltage is applied to the grids of the power tubes 156, giving the desired control of pulse amplitude. Tubes 156 are of ceramic type, examples having the catalogue numbers 4C x 250B, and products of Amperex Corporation. They have been found to be exceptionally capable of handling substantial changes in load current, resulting from movement of a patient's body 180 (in FIG. 2) relatively toward and away from the head 12. A regulated power supply for the tubes is shown in FIG. 6 at 260, and includes a gas regulator tube VR02, transformer 261, rectifier bridge 262, and filter 263.

In FIG. 5, scalers 172 and 176 are electrically interconnected, as by lead 210. Scalers 141 and 176 are typically mechanically operated simultaneously as by mounting on a common shaft, so that an adjustment of the scaler 141 to change pulse interval simultaneously changes the pulse amplitude, due to the connection of scalers 172 and 176. The purpose of this cross-over connection is to minimize changes in selected pulse amplitude in response to changing the selected pulse interval. For this purpose, scaler 176 is similar to the scaler 172 previously described in that it includes a series of resistors R93-R103 which are tapped at intermediate points for selective connection to rotary terminal 175, placing a desired member of resistors in the circuit.

Finally, reference to FIG. 5 shows a meter 196 connected to both the pulse interval and pulse amplitude controls, in order that the meter will sense changes in both these controls. Meter 196 is connected with scalers 141 and 172 as by means of path that includes rotary terminals 175' and 175 of scaler 176 (operated mechanically with scaler 141), lead 199, rotary terminals 220' and 220 of scaler 222 (operated mechanically with scaler 172) and leads 223 and 224 connecting with voltage source C1. Thus, adjustment of either scaler 141 and 172 will affect adjustment of the meter to show that pulse amplitude and interval controls are working.

FIG. 4 also shows the provision of a tank circuit 260 connected between the parallel tube outputs 261 and the primary coil 25. Circuit 260 includes variable capacitor 262 and an inductor 263 having a grounded end terminal 264. The inductor has in intermediate tap 265 connected with the head primary coil 25 via center conductor 55 of cable 14. Circuit 260 provides bent impedance match as between the power stage 117 and the treatment head.

In the above, the duty factor of about 0.45 is arrived at by providing a pulse repetition rate of about 3000 pps and a pulse duration of about 150 microseconds.

I claim:

1. Improved electrotherapeutic apparatus comprising
   a. an electromagnetic energy radiating head including primary and secondary coils and a capacitor electrically connected across the secondary coil,
   b. and input circuit means connected with the primary coil of the head and including a source of high frequency oscillations, power amplifier means, and control means for creating and transmitting to the primary coil of the head a sequence of pulses of high frequency electrical energy and for controlling the amplitude of the pulses and the intervals therebetween, the pulses having substantially rectangular shape and having a repetition rate and duration characterized in that they define a duty factor of between 0.35 and 0.55, where
   (duty factor) = (pulse repetition rate in pulses per second) × (pulse duration in micro seconds)
   c. said power amplifier means being electrically connected in series sequence with said source of high frequency oscillations, said power amplifier means including at least four ceramic type vacuum tubes having parallel outputs producing said substantially rectangular pulses.

2. The apparatus of claim 1 wherein said duty factor is about 0.45.

3. The apparatus of claim 1 wherein said control means includes means to produce pulses per second ≅ 3000 and pulse duration ≅ 150 microseconds.

4. The apparatus of claim 1 wherein said input circuit means includes a series resonant circuit at the oscillatory signal input to said tubes.

5. Improved electrotherapeutic apparatus, comprising
   a. an electromagnetic energy radiating head including primary and secondary coils and a capacitor electrically connected across the secondary coil,
   b. and input circuit means connected with the primary coil of the head and including a source of high frequency oscillations, power amplifier means, and control means for creating and transmitting to the primary coil of the head a sequence of pulses of high frequency electrical energy and for controlling the amplitude of the pulses and the intervals therebetween, said source and amplifier means being connected, said pulses having substantially rectangular shape, c. said power amplifier means comprising at least four ceramic type vacuum tubes, said tubes having parallel outputs each connected in series with the input to said primary coil, the oscillatory signal input to the tubes being connected to the tube grids.

6. The apparatus of claim 5 wherein said power amplifier means includes a series resonant circuit at the oscillatory signal input to the tubes.

7. The apparatus of claim 6 wherein said control means includes a pulse duration control circuit connected with the screens of all of said tubes, said circuit including a voltage controlling variable resistor directly connected in series with said screens.

8. The apparatus of claim 5 including a tank circuit connected between the outputs of said tubes and the primary coil, said tank circuit including a variable capacitor and an inductor having a grounded end terminal, the inductor having an intermediate tap connected with said primary coil.

* * * * *